United States Patent [19]
Ochiai et al.

[11] 4,251,657
[45] Feb. 17, 1981

[54] METHOD FOR REMOVING PROTECTIVE GROUPS

[75] Inventors: Michihiko Ochiai, Suita; Akira Morimoto, Ikeda; Toshio Miyawaki, Nishinomiya, all of Japan

[73] Assignee: Takeda Chemical Industries, Ltd., Osaka, Japan

[21] Appl. No.: 966,753

[22] Filed: Dec. 5, 1978

[30] Foreign Application Priority Data

Dec. 9, 1977 [JP] Japan ................. 52-148414

[51] Int. Cl.³ ............................................ C07D 501/36
[52] U.S. Cl. ....................................... 544/027; 544/16; 544/30; 548/193; 548/194; 260/245.2 R; 260/239.1; 544/28
[58] Field of Search ................... 544/30, 28, 16, 27; 260/239.1, 245.2; 548/193, 194

[56] References Cited

FOREIGN PATENT DOCUMENTS 836813 6/1976 Belgium.
853545 10/1977 Belgium.

OTHER PUBLICATIONS

Cocker et al., J. Chem. Soc. pp. 5015–5030 (1968).
J. A. C. S. vol. 90 4508 (1968).

Primary Examiner—Nicholas S. Rizzo
Attorney, Agent, or Firm—Wenderoth, Lind & Ponack

[57] ABSTRACT

A halogenoacetyl group is removed from a halogenoacetyl amino compound in a short period of reaction time by reacting the halogenoacetyl amino compound with an N-substituted dithiocarbamic acid or a salt thereof.

8 Claims, No Drawings

METHOD FOR REMOVING PROTECTIVE GROUPS

The present invention relates to an improved method for removing protecting groups.

More particularly, the improvement lies in employing a N-substituted dithiocarbamic acid or a salt thereof in place of thiourea in the production of an amino compound by removing a halogenoacetyl group from the corresponding halogenoacetyl amino compound.

In the field of chemical reactions, it is a common practice, when it is feared that the amino group of a starting material will to undergo undesirable attack by another reagent, to protect it with a suitable protective group prior to subjecting the starting material to an intended reaction, and then, after completion of the reaction, to remove the protective group to obtain the desired amino compound.

As one of such protective groups, halogenoacetyl is known to be excellent. However, removal of the halogenoacetyl group requires relatively severe conditions. For example, treatment with 10 N-hydrochloric acid and glacial acetic acid [Chemical Abstract 50, 15419h (1956)]or treatment with alcoholic HCl [Zeitschrift für Naturforschung 6b, 340 (1951)]has been conventionally practiced. These treatments are disadvantageous in that where an unstable group exists in the substrate molecule, the compound cannot be safely subjected to such severe conditions. It has recently been discovered that if a halogenoacetyl amino compound is reacted with thiourea, the halogenoacetyl group may be removed via amidinolysis under milder conditions, thus showing that the process is applicable to unstable compounds [J. Am. Chem. Soc. 90, 4508(1968); J. Chem. Soc. 1965, 5015]. However, this removal reaction using thiourea has the disadvantage that, in many cases, the S-substituted thioformamidine hydrochloride

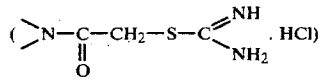

produced as a reaction intermediate must be heated in the presence of water in order to convert the intermediate into the desired amino compound, exerting a bad influence on the desired amino compound. The reaction of halogenoacetyl amino compounds and thiourea forms the desired amino compound as well as 2-iminothiazolidone through intramolecular amidinolysis. In cases where the solubility of the desired amino compound is similar to that of 2-iminothiazolidone, it is quite difficult to separate the two compounds from each other.

To overcome the shortcomings of the prior art, we have conducted research and have unexpectedly found that removal of the protective group in the present invention proceeds in shorter periods of reaction time than the known method using thiourea.

We have also found that solubility of N-substituted rhodanine (i.e. a byproduct corresponding to 2-iminothiazolidone) may be modified by changing the kind of the substituent of the N-substituted dithiocarbamate, taking the solubility of the desired amino compound into consideration. Therefore, the present invention facilitates the recovery of the desired amino compound from the reaction mixture.

More fundamentaly, the N-substituted rhodanine is generally soluble in organic solvents and the desired amino compound, particularly a cephem or penam compound having an amino group, is soluble in water. Therefore, the amino compound can be easily separated from the byproduct.

Therefore, it is the main object of the present invention to provide an industrially feasible method for producing an amino compound by removing a halogenoacetyl group from a halogenoacetyl amino compound.

The amino compound is intended to mean an organic compound containing one or more amino groups in the molecule.

As examples of said amino compound, there may be mentioned aliphatic amino compounds, aromatic amino compounds, five- to six-membered hetero-aromatic amino compounds, alicyclic amino compounds, amino acids, carbamoyl compounds, etc. Stated differently, said amino compound is exemplified by straight-chain alkanes, branched or straight-chain alkenes, saturated or unsaturated cycloalkanes, aromatic hydrocarbons, or 5- to 6-membered heterocyclic compounds e.g. furan, thiophene, pyrroline, thiazole, oxazole, thiadiazole, oxadiazole, diazole, triazole, tetrazole, pyridine, pyrimidine, pyridazine, etc.), which have amino groups as substituents. In addition to one or more amino groups, these compounds may have one or more groups inert to the reaction such as hydroxyl, carboxyl, nitro, halogen, nitroso, alkyl, alkenyl, cycloalkyl, aryl, aralkyl and heterocyclic groups. The method according to this invention is particularly suitable for amino compounds containing a cephem or penam ring, which is comparatively unstable. Such compounds are those of the formulas:

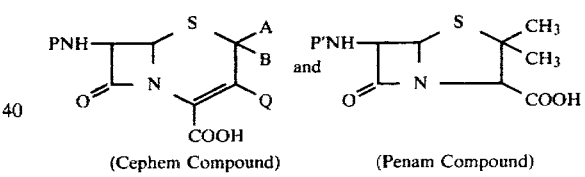

(Cephem Compound)    (Penam Compound)

as well as their pharmaceutically acceptable salts, in which each of A and B is hydrogen or methyl, each of P and P' is an organic acyl group constituting a cephalosporin antibiotic or a penicllin antibiotic, Q is hydrogen or a substituent which constitutes a cephalosporin antibiotic, and at least one of P and Q has an amino group as a substituent and P' has an amino group as a substituent.

In the above general formulas, P is exemplified by 2-(2-aminothiazol-4-yl)-2-(syn)-methoximinoacetyl, α-aminophenylacetyl, α-sulfo-p-aminophenylacetyl, α-amino-p-hydroxyphenylacetyl, etc. P' is exemplified by α-aminophenylacetyl, α-sulfo-p-aminophenylacetyl, α-amino-p-hydroxyphenylacetyl, etc.

Q is exemplified by hydrogen, (1-methyl-1H-tetrazol-5-yl)thiomethyl, carbamoyloxymethyl, acetoxymethyl, methyl, 5-acetylamino-1,3,4-thiadiazol-2-yl, (2-methyl-thiadiazol-5-yl)thiomethyl, hydroxymethyl, methoxy, (1-carboxymethyl-1H-tetrazol-5-yl)thiomethyl. Examples of such amino-containing cephem compounds includes 7-amino-3-carbamoyloxymethyl-3-cephem-4-carboxylic acid, 7-[2-(2-aminothiazol-4-yl)-2-(syn)-methoxyiminoacetamido]-3-carbamoyloxymethyl-3-cephem-4-carboxylic acid, 7-(5-carboxy-5-aminovaleramido)-3-carbamoyloxymethyl)-3-cephem- 4-carboxylic acid, 7-[2-(2-aminothiazol-4-yl)-2-(syn)-methoxyiminoacetamido]cephalosporanic acid, 7-[2-(2-aminothiazol-4-yl)-2-(syn)-methoxyiminoacetamido]-3-(1-methyl-1H-tetrazol-5-yl)thiomethyl-3-cephem-4-carboxylic acid, 7-[2-(2-aminothiazol-4-yl)-2-(syn)-methoxyiminoacetamido]desacetoxycephalosporanic acid, benzhydryl 7-(2-thienylacetylamido)-3-carbamoyloxymethyl-3-cephem-4-carboxylate, 7-[2-(2-aminothiazol-4-yl)-2-(syn)-methoxyimonoacetamido]-3-cephem-4-carboxylic acid, etc. as well as their pharmaceutically acceptable salts. The pharmaceutically acceptable salts are exemplified by alkali metal (e.g. sodium) salts, organic amine (e.g. triethylamine) salts or other salts in cephalosporin antibiotics and penicillin antibiotics.

According to the present invention, the protective group, i.e. a halogenoacetyl group is removed from a halogenoacetyl amino compound to produce the desired amino compound.

The halogenoacetyl group is exemplified by chloroacetyl, bromoacetyl, fluoroacetyl, etc., but chloroacetyl and bromoacetyl are preferred.

The starting material of the present invention (i.e. a halogenoacetyl amino compound) is a compound having a halogenoacetyl amino group, $XCH_2CO-NH-$ in which X is a halogen, in the molecule, i.e. an amino compound of which amino group is protected by a halogenoacetyl.

The other reagent in the reaction is an N-substituted dithiocarbamic acid of the formula:

$$R'NHCSH \atop \overset{S}{\|}$$

or a salt thereof, and the salt is preferred for the reaction of the present invention.

The substituent R' is exemplified by a lower alkyl group of 1 to 6 carbon atoms (such as methyl, ethyl, n-propyl, n-butyl, etc.); a cycloalkyl group of 5 to 7 carbon atoms (such as cyclohexyl, methylcyclohexyl, etc.); an aralkyl group of 7 to 10 carbon atoms (such as benzyl, methoxybenzyl, methylbenzyl, etc.); and an aryl group of 6 to 10 carbon atoms (such as phenyl, tolyl, methoxyphenyl, etc.).

The salt of N-substituted dithiocarbamic acid is exemplified by a corresponding alkali metal salt, alkaline earth metal salt, ammonia salt and organic amine salt. The alkali metal includes sodium, potassium, etc., alkaline earth metal includes calcium, magnesium, etc., and the organic amine includes trimethylamine, monomethylamine, trimethylamine, diethylamine, monoethylamine, n-propylanine, cyclohexylamine, benzylamine, aniline, N,N-dimethylaniline, etc.

The reaction according to this invention proceeds as follows:

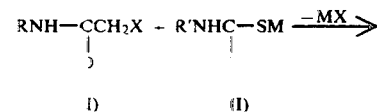

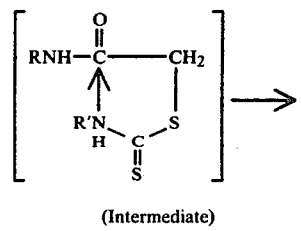

(Intermediate)

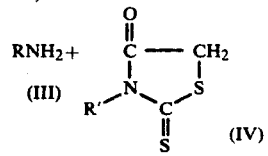

Compound (I): a halogenoacetyl amino compound
Compound (II): an N-substituted dithiocarbamic acid or its salt
Compound (III): a desired amino compound
Compound (IV): an N-substituted rhodanine (byproduct)

Normally this reaction is carried out by reacting a compound (I) having a halogenoacetyl amino group with an N-substituted dithiocarbamic acid or a salt thereof (II). The reaction may generally be carried out smoothly in a solvent which may be any optional solvent as long as it does not exert any bad influence on the reaction. Thus, for example, water, alcohols such as methanol, ethanol, propanol, etc., ethers such as diethyl ether, tetrahydrofuran, dioxane, etc.; halogenated hydrocarbons such as chloroform, methylene chloride, dichloroethylene, dichloroethane, etc. and esters such as ethyl acetate, butyl acetate, etc., dimethylsulfoxide, N,N-dimethylformamide, N,N-dimethylacetamide, etc. as well as mixtures of such solvents, may be mentioned by way of example.

The amount of the compound (II) relative to the compound (I) is optional but it is usually in the range of from 0.5 to 3 mols, preferably 0.8 to 1.3 mols per mol of the compound (I).

The reaction temperature is usually in the range of from $-20°$ C. to $100°$ C., preferably in the range of from $-10°$ C. to $50°$ C.

The byproduct, N-substituted rhodanine derivative (IV) formed by a kind of aminolysis is a substance generally soluble in organic solvents and can be easily separated from the reaction mixture. The amino-compound ($RNH_2$) obtained on removal of the protective group is isolated and purified by procedures known in the art general organic chemistry, such as extraction, crystallization, distillation, chromatography, etc.

The N-substituted dithiocarbamic acid or salt which is employed in the reaction according to this invention can be produced by the known process or any process analogous thereto. [cf. Rodds: Chemistry of Carbon Compounds, Vol. 1, Part C, p. 331 (1965)]. The compound having a halogenoacetyl amino group can be easily produced by applying the known amidation process [cf. R. B. Wagner, H. D. Zook: Synthetic Organic Chemistry, p. 566 (1955)] or any process analogous thereto, to such an amino-containing compound.

EXAMPLE 1

In 15 ml of water was suspended 1.75 g of 7-amino-3-(N-chloroacetylcarbamoyloxymethyl)-3-cephem-4-carboxylic acid and the suspension was stirred. Sodium hydrogen carbonate (0.42 g) was added to obtain a solution. After adding 1.1 g of sodium N-methyldithiocarbamate, the mixture was stirred at room temperature for 1.5 hours. The crystals were collected by filtration, rinsed with water and dried. Recrystallization from diethyl ether gave crystals of N-methylrhodanine, m.p. 71°–72° C. (literature 72° C., Anlreash: Monatshefte für Chemie 25, 167). The first filtrate after filtration of N-methylrhodanine was adjusted to pH 3.5 with N-hydrochloric acid and allowed to stand under icecooling for one hour. The precipitate was collected by filtration, washed with water, methanol and diethyl ether in the order mentioned and dried. By the above procedure there was obtained 1.06 g of 7-amino-3-carbamoyloxymethyl-3-cephem-4-carboxylic acid as white powders. UV (pH 6.5, phosphate): λmax 265 nm ($\epsilon$ 7885). NMR (d$_6$-PMSO): 3.34, 3.57 ppm (2H, ABq, 2—CH$_2$), 4.58, 4.87 ppm (2H, ABq, 3—CH$_2$), 4.76 ppm (1H, d, 6-H), 4.96 ppm (1H, d, 7-H), 6.50 ppm (2H, bs, —OCONH$_2$).

Elemental analysis, for C$_9$H$_{11}$N$_3$O$_5$S.0.5H$_2$O: Calcd. C, 38.29; H, 4.29; N, 14.89; Found: C, 38.84; H, 4.25; N, 14.12.

EXAMPLE 2

In 10 ml of water was suspended 1.6 g of 7-[2-(2-chloroacetamidothiazol-4-yl)-2-(syn)-methoxyiminoacetamido]-3-(N-chloroacetylcarbamoyloxymethyl)-3-cephem-4-carboxylic acid, and with stirring, sodium hydrogen carbonate was added to adjust the pH to 7.0. Then, after addition of 0.80 g of sodium N-methyldithiocarbamate, the mixture was stirred at room temperature for one hour. The reaction mixture was washed with ethyl acetate and the water layer was taken and purified by column chromatography on Amberlite XAD-2(trademark, Rohm & Haas Co.). By the above procedure there was obtained 650 mg of sodium 7-[2-(2-aminothiazol-4-yl)-2-(syn)-methoxyiminoacetamido]-3-carbamoyloxymethyl-3-cephem-4-carboxylate as white powders.

Elemental analysis, for C$_{15}$H$_{15}$N$_6$O$_7$S$_2$Na.3H$_2$O: Calcd. C, 33.84; H, 3.98; N, 15.78; Found C, 33.94; H, 3.82; N, 15.42.

NMR(60 MHz, D$_2$O): 3.47 ppm (2H, q, 2—CH$_2$), 3.92 ppm (3H, s, OCH$_3$), 4.68 ppm (2H, q, —CH$_2$—OCONH), 5.27 ppm (1H, d, 6-H), 5.72 ppm (1H, d, 7-H), 6.95 ppm (1H, s, thiazole 5-H).

EXAMPLE 3

In 600 ml of dichloromethane was dissolved 164.5 g of 7-(5-carboxy-5-phthalimidovaleramido)-3-hydroxymethyl-3-cephem-4-carboxylic acid ditriethylamine salt. After the solution was cooled to an internal temperature of 0° to −5° C., a solution of 105 g of chloroacetyl isocyanate in 100 ml of dichloromethane was added dropwise. After the dropwise addition, the mixture was stirred for 30 minutes and 600 ml of water was added dropwise to the reaction mixture, followed by stirring for 20 minutes. The reaction mixture was separated into layers and the upper layer was taken. By this procedure there was obtained an aqueous solution of 7-(5-carboxy-5-phthalimidovaleramido)-3-(N-chloroacetylcarbamoyloxymethyl)-3-cephem-4-carboxylic acid ditriethylamine salt.

To this solution was added 64.1 g of sodium N-methyldithiocarbamate and the mixture was stirred at room temperature for one hour, after which it was washed with ethyl acetate and the water layer was taken. This aqueous solution was adjusted to pH 2.0 with phosphoric acid and extracted with a mixture of ethyl acetate and tetrahydrofuran. The extract was washed with saturated aqueous sodium chloride and dried over magnesium sulfate. The solvent was distilled off under reduced pressure and the viscous oily residue thus obtained was treated with diethyl ether. The powders thus obtained were dried under reduced pressure over phosphorus pentoxide. By the above procedure there was obtained 126.5 g of 7-(5-carboxy-5-phthalimidovaleramido)-3-carbamoyloxymethyl-3-cephem-4-carboxylic acid.

NMR(d$_6$-DMSO): 1.26–2.36 ppm (6H, m, —(CH$_2$)$_3$—), 3.45 ppm (2H, ABq, 2—CH$_2$), 4.74 ppm (1H, t,

4.77 ppm (2H, ABq, 3—CH$_2$), 5.06 ppm (1H, d, 6-H), 5.62 ppm (1H, dd, 7-H), 6.56 (2H, s, CONH$_2$), 7.92 ppm (4H, s, aromatic ring-H).

EXAMPLE 4

In 1 l of dichloromethane was suspended 254 g of 7-[5-carboxy-5-(p-t-butylbenzamido)valeramido]-3-hydroxymethyl-3-cephem-4-carboxylic acid monotriethylamine salt, and with stirring, 20.1 g of triethylamine was added at room temperature to obtain a solution. The solution thus obtained was cooled to an internal temperature of 0° to −5° C. and 96 g of chloroacetyl isocyanate dissolved in 100 ml of dichloromethane was added dropwise. After the dropwise addition had been completed, the mixture was stirred for 20 minutes, at the end of which 1 l of water and 20.1 g of triethylamine were added. The mixture was stirred for 10 minutes, after which it was separated into layers and the water layer was taken. By the above procedure there was obtained an aqueous solution containing 7-[5-carboxy-5-(p-t-butylbenzamido)valeramido]-3-(N-chloroacetylcarbamoyloxymethyl)-3-cephem-4-carboxylic acid di-triethylamine salt. To this solution was added 88 g of sodium N-methyldithiocarbamate and the mixture was stirred at room temperature for 1.5 hours. The reaction mixture was washed twice with 500 ml portions of ethyl acetate, followed by addition of 500 ml of tetrahydrofuran and 500 ml of ethyl acetate. The mixture was adjusted to pH 2.0 with phosphoric acid and, after thorough shaking, the organic layer was taken, washed with saturated aqueous sodium chloride and dried over magnesium sulfate. The solvent was distilled off under reduced pressure, the viscous oily residue was treated with diethyl ether and the resultant powders were dried under reduced pressure over phosphorus pentoxide. By the above procedure there was obtained 169 g of 7-[5-carboxy-5-(p-t-butylbenzamido)valeramido]-3-carbamoyloxymethyl-3-cephem-4-carboxylic acid. A 5.7 g portion of the above product was taken, suspended in 15 ml of water and dissolved by the addition of 2.1 g of triethylamine. The solution was purified by column chromatography on Amberlite XAD-2 and Sephadex LH-20 (trademark, Pharmacia Fine Chemicals Co.). By the above procedure there was obtained 2.6 g of 7-(5-carboxy-5-(p-t-butylbenzamido)valeramido]-3-carbamoyloxymethyl-3-cephem-4-carboxylic acid di-triethylamine salt. Elemental analysis, for $C_{36}H_{62}N_6O_9S \cdot H_2O$: Calcd. C, 57.26; H, 8.09; N, 10.54; Found C, 57.17; H, 8.41; N, 10.38.

NMR($d_6$-DMSO): 1.13 ppm (18H, t, N(CH$_2$CH$_3$)$_3$), 1.31 ppm (9H, s, t-Bu), 1.4–2.0 ppm (4H, m, (CH$_2$)$_2$), 3.17, 3.48 ppm (2H, ABq, 2—CH$_2$), 4.24 (1H, m,

—CH), 4.66, 4.87 ppm (2H, ABq, 3—CH$_2$), 4.94 ppm (1H, d, 6-H), 5.50 ppm (1H, dd, 7-H), 6.44 ppm (2H, bs, CONH$_2$), 7.46 ppm (2H, d, aromatic ring-H), 7.79 ppm (2H, d, aromatic ring-H).

EXAMPLE 5

In 150 ml of water was suspended 9.73 g of 7-[2-(2-chloroacetamidothiazol-4-yl)-2-(syn)-methoxyiminoacetamido]-3-carbamoyloxymethyl-3-cephem-4-carboxylic acid, which was dissolved by the addition of 1.55 g of sodium hydrogen carbonate with stirring. Then, after addition of 2.6 g of sodium N-methyldithiocarbamate, the mixture was stirred at room temperature for one hour. The reaction mixture was washed twice with 50 ml portions of ethyl acetate and the water layer was degassed and purified by column chromatography on Amberlite XAD-2. By the above products there was obtained 5.1 g of sodium 7-[2-(2-aminothiazol-4-yl)-2-(syn)-methoxyiminoacetamido]-3-carbamoyloxymethyl-3-cephem-4-carboxylate as white powders.

This product was identical with the compound obtained according to Example 2.

EXAMPLE 6

In 7 ml of water was suspended 2.4 g of 7-[2-(2-chloroacetamidothiazol-4-yl)-2-(syn)-methoxyiminoacetamido]-cephalosporanic acid and, with stirring, 384 mg of sodium hydrogen carbonate was added. To the solution thus obtained was added 650 mg of sodium N-methyldithiocarbamate and the mixture was stirred at room temperature for one hour. The reaction mixture was washed with ethyl acetate and the water layer was purified by column chromatography on Amberlite XAD-2. By the above procedure there was obtained 2.11 g of 7-[2-(2-aminothiazol-4-yl)-2-(syn)-methoxyiminoacetamido]cephalosporanic acid as white powders.

Elemental analysis, for $C_{16}H_{16}N_5O_7S_2Na \cdot 2.5H_2O$: Calcd. C, 36.78; H, 4.05; N, 13.40; Found C, 36.93; H, 3.80; N, 12.68.

NMR(60 MHz, D$_2$O): 2.07 ppm (3H, s, COCH$_3$), 3.53 ppm (2H, q, 2—CH$_2$), 3.98 ppm (3H, s, OCH$_3$), 4.75 ppm (2H, q, 3—CH$_2$, 5.21 ppm (1H, d, 6-H), 5.81 ppm (1H, d, 7-H), 7.01 ppm (1H, s, thiazole 5-H).

EXAMPLE 7

In 6.5 ml of water was suspended 1.6 g of 7-[2-(2-chloroacetamidothiazol-4-yl)-2-(syn)-methoxyiminoacetamido]-3-(1-methyl-1H-tetrazol-5-yl)thiomethyl-3-cephem-4-carboxylic acid, which was dissolved by addition of 250 mg of sodium hydrogen carbonate with stirring. Then, after addition of 415 mg of sodium N-methyldithiocarbamate, the mixture was stirred at room temperature for one hour. The reaction mixture was washed with ethyl acetate and the water layer was purified by column chromatography on Amberlite XAD-2. By the above procedure there was obtained 714 mg of sodium 7-[2-(2-aminothiazol-4-yl)-2-(syn)-methoxyiminoacetamido]-3-(1-methyl-1H-tetrazol-5-yl)thiomethyl-3-cephem-4-carboxylate as white powders.

Elemental analysis for $C_{16}H_{16}N_9O_5S_2Na \cdot 2H_2O$: Calcd. C, 33.74; H, 3.54; N, 22.13; Found C, 34.18; H, 3.57; N, 21.79.

NMR(60 MHz, D$_2$O): 3.59 ppm (2H, q, 2-CH$_2$), 3.93 ppm (3H, s, OCH$_3$), 3.98 ppm (3H, s, N-CH$_3$), 4.18 ppm (2H, q, 3-CH$_2$), 5.12 ppm (1H, d, 6-H), 5.72 ppm (1H, d, 7-H), 6.93 ppm (1H, s, thiazole 5-H).

EXAMPLE 8

In 250 ml of water was suspended 28.5 g of 7-[2-(2-chloroacetamidothiazol-4-yl)-2-(syn)-methoxyiminoacetamido]-desacetoxycephalosporanic acid, which was then dissolved by adding of 5.05 g of sodium hydrogen carbonate with stirring. Then, after addition of 9.42 g of sodium N-ethyldithiocarbamate, the mixture was stirred at room temperature for 1.5 hours. The reaction mixture was washed with ethyl acetate and the water layer was purified by column chromatography on Amberlite XAD-2. By the above procedure there was obtained 18.0 g of sodium 7-[2-(2-aminothiazol-4-yl)-2-(syn)-methoxyimonoacetamido]desacetoxycephalosporanate as white powders.

Elemental analysis, for $C_{14}H_{14}N_5O_5S_2Na \cdot 1.5H_2O$: Calcd. C, 37.67; H, 3.84; N, 15.68; Found C, 37.37; H, 3.98; N, 15.38.

NMR(60 MHz, D$_2$O): 1.94 ppm (3H, s, 3-CH$_3$), 3.46 ppm (2H, q, 2-CH$_2$), 4.00 ppm (3H, s, OCH$_3$), 5.17 ppm (1H, d, 6-H), 5.76 ppm (1H, d, 7-H), 6.99 ppm (1H, s, thiazole 5-H).

EXAMPLE 9

In a mixture of 18 ml of water and 6 ml of tetrahydrofuran was dissolved 4.58 g of monosodium 7-(5-carboxy-5-aminovaleramido)-3-hydroxymethyl-3-cephem-4-carboxylate. While the solution was adjusted to pH 8.0–9.0 by the addition of 3N-aqueous sodium hydroxide, 6 ml of a tetrahydrofuran solution containing 2.12 g of p-t-butylbenzoyl chloride was added dropwise. After the dropwise addition had been completed, the mixture was further stirred for 30 minutes and, then, adjusted to pH 2.5 with phosphoric acid. The solution was extracted with a mixture of dichloromethane and tetrahydrofuran. The extract was washed with saturated aqueous sodium chloride and dried over magnesium sulfate. The solvent was distilled off and the residue was dissolved by addition of 50 ml of dichloromethane and 2.8 ml of triethylamine. The solution was concentrated under reduced pressure, the residue was dissolved by addition of 80 ml of dichloromethane and the solution was concentrated under reduced pressure. The above operation was further repeated twice, whereupon 7-[5-carboxy-5-(p-t-butylbenzamido)-valeramido]-3-hydroxymethyl-3-cephem-4-carboxylic acid ditriethylamine salt was obtained. This product was dissolved in 60 ml of dichloromethane containing 3.2 ml of triethylamine and the solution was cooled to an internal temperature of −5° to −10° C. With stirring, 10 ml of dichloromethane containing 3.0 g of chloroacetyl isocyanate was added dropwise. After the dropwise addition had been completed, the mixture was further stirred for 20 minutes to obtain a dichloromethane solution containing 7-[5-carboxy-5-(p-t-butylbenzamido)valeramido]-3-(N- chloroacetylcarbamoyloxymethyl)-3-cephem-4-carboxylic acid di-triethylamine salt. This reaction mixture was cooled to −20° C. and 3.26 g of trimethylchlorosilane was added in a single dose. The mixture was stirred at −10° C. for one hour. It was cooled to −30° C. and 3 ml of N,N,-dimethylaniline and 4.2 g of phosphorus pentachloride were added. The mixture was maintained at an internal temperature of −20° to −30° C. After stirring the mixture at that temperature, for 2 hours, 37 ml of methanol was added dropwise at an internal temperature of no more than −30° C. After the dropwise addition had been completed, the mixture was stirred at −5° C. for 25 minutes, at the end of which time 22 ml of water was added. The pH was adjusted to 3.5 with aqueous ammonia, whereupon 7-amino-3-(N-chloroacetylcarbamoyloxymethyl)-3-cephem-4-carboxylic acid separated. Without isolating the precipitate, the reaction mixture was adjusted to pH 6.5 by the addition of 3N-aqueous sodium hydroxide. Then, after addition of 2 g of sodium N-methyldithiocarbamate, the mixture was stirred at room temperature for one hour. It was then adjusted to pH 3.5 with hydrochloric acid and allowed to stand under ice-cooling. The resultant precipitate was collected by filtration, washed with water and methanol and dried. By the above procedure there was obtained 1.13 g of 7-amino-3-carbamoyloxymethyl-3-cephem-4-carboxylic acid as white powders. This product was identical with the product obtained according to Example 1.

EXAMPLE 10

In a mixture of 7 ml of methanol and 10 ml of tetrahydrofuran, there was dissolved 204 mg of p-nitro-N-chloroacetylaniline.

To the solution was added 180 mg of sodium N-methyldithiocarbamate and the mixture was stirred at room temperature for 2 hours. The reaction mixture was concentrated under reduced pressure and the residue was dissolved in ethyl acetate and extracted with 5% HCl. The extract was neutralized with sodium hydrogen carbonate and extracted with ethyl acetate. The organic layer was washed with water and dried over magnesium sulfate. The solvent was distilled off and the residue was recrystallized from diethyl ether. By the above procedure there was obtained 105 mg of p-nitroaniline. m.p. 145°–146° C.

EXAMPLE 11

In 16 ml of tetrahydrofuran was dissolved 1 g of 2-(2-chloroacetamidothiazol-4-yl)-2-(syn)-methoxyiminoacetic acid, followed by addition of 0.93 g of sodium N-methyldithiocarbamate. The mixture was stirred at room temperature for 2 hours. The precipitate was collected by filtration and washed with a small amount of tetrahydrofuran, followed by addition of 15 ml of water. The precipitate dissolved once and crystals were then formed. Those crystals were collected by filtration (0.7 g) and recrystallized from aqueous ethanol. By the above procedure there was obtained 2-(2-aminothiazol-4-yl)-2(syn)-methoxyiminoacetic acid as colorless needles, m.p. 164.6° C.

Elemental analysis, for $C_6H_7N_3O_3S.1.5H_2O$: Calcd. C, 31.57; H, 4.41; N, 18.41; Found C, 31.44; H, 4.32; N, 18.35.

NMR spectrum (90 MHz, $D_2O$ containing $NaHCO_3$): 3.96 ppm (s, 3H, $OCH_3$), 6.91 ppm (s, 1H, thiazole 5-H).

EXAMPLE 12

2-(2-chloroacetamidothiazol-4-yl)-2-(anti)-methoxyiminoacetic acid was reacted in the same manner as Example 11 to obtain 2-(2-aminothiazol-4-yl)-2-(anti)-methoxyiminoacetic acid as pale yellow crystals, m.p. 168.0° C.

Elemental analysis, for $C_6H_7N_3O_3S$: Calcd. C, 35.81; H, 3.50; N, 20.88; Found C, 35.71; H, 3.40; N, 20.83.

NMR spectrum (90 MHz, $D_2O$ containing $NaHCO_3$): 4.03 ppm (s, 3H, $OCH_3$), 7.46(s, 1H, thiazole 5-H).

EXAMPLE 13

In 5 ml of tetrahydrofuran was dissolved 640 mg of benzhydryl 7-(2-thienylacetamido)-3-(N-chloroacetylcarbamoyloxymethyl)-3-cephem-4-carboxylate, followed by addition of 260 mg of sodium N-methyldithiocarbamate dissolved in 2 ml of water. The mixture was stirred at room temperature for 4 hours. A major portion of the tetrahydrofuran was distilled off and the residue was extracted with chloroform. The chloroform layer was washed with water, dried and concentrated. The residue was chromatographed on silica gel, elution being carried out with chloroform-ethyl acetate (2:1). By the above purification procedure there was obtained benzhydryl 7-(2-thienylacetamido)-3-carbamoyloxymethyl-3-cephem-4-carboxylate as white powders.

Elemental analysis, for $C_{28}H_{25}N_3O_6S_2$: Calcd. C, 59.67; H, 4.47; N, 7.45; Found C, 59.10; H, 4.34; N, 7.32.

NMR spectrum (60 MHz, $d_6$-DMSO-deuteriochloroform); 3.50 ppm (bs. 2H, 2-$CH_2$), 3.86 ppm(s, 2H,

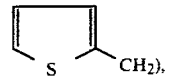

4.95 ppm (bs, 2H,

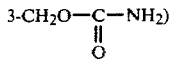

3-$CH_2O-C-NH_2$)
$\phantom{3-CH_2O-}\|$
$\phantom{3-CH_2O-}O$

What is claimed is:

1. In the method for removing the halogenoacetyl group from a compound having in the molecule a halogenoacetyl amino group $XCH_2CO-NH$ in which X is halogen which comprises reacting the halogenoacetyl amino compound with an agent capable of effecting removal of the halogenoacetyl group, the improvement according to which the agent capable of effecting removal of the halogenoacetyl group is an N-substituted dithiocarbamic acid or an alkali metal, alkaline earth metal, ammonia or organic amine salt thereof wherein the substituent is selected from the group consisting of lower alkyl of 1 to 6 carbon atoms, cycloalkyl of 5 to 7 carbon atoms, and aralkyl of 7 to 10 carbon atoms or aryl of 6 to 10 carbon atoms the reaction being conducted in an inert solvent, at a temperature of from −20° C. to 100° C. and wherein 0.5 to 3 mol of the N-substituted dithiocarbamic acid as salt thereof are present per 1 mol of the halogenoacetyl amino compound.

2. A method as claimed in claim 1, wherein the substituent of the N-substituted dithiocarbamic acid or salt thereof is alkyl of 1 to 4 carbon atoms or cycloalkyl of 5 to 7 carbon atoms.

3. A method as claimed in claim 1, wherein the halogenoacetyl amino compound is a compound of the formula

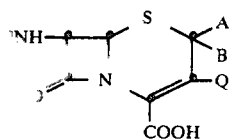

wherein P is an organic acyl having a halogenoacetyl amino group, each of A and B is hydrogen or methyl, and Q is hydrogen, methyl, acetoxymethyl, carbamoyloxymethyl, (1-methyl-1H-tetrazol-5-yl)-thiomethyl, 5-acetylamino-1,3,4-thiadiazol-2-yl, or a pharmaceutically acceptable salt thereof.

4. A method as claimed in claim 3, wherein 7-[2-(2-chloroacetamidothiazol-4-yl)-2-(syn)-methoxyiminoacetamido]-3-(1-methyl-1H-tetrazol-5-yl)thiomethyl-3cephem-4-carboxylic acid or an alkali metal or amine salt thereof is reacted with an N-methyldithiocarbamic acid alkali metal salt or an N-ethyldithiocarbamic acid alkali metal salt.

5. A method as claimed in claim 3, wherein 7-[2-(2-chloroacetamidothiazol-4-yl)-2-(syn)-methoxyiminoacetamidol]-3-(1-methyl-1H-tetrazol-5-yl)thiomethyl-3-cephem-4-carboxylic acid sodium salt is reacted with sodium N-methyldithiocarbamate.

6. A method as claimed in claim 1, wherein 2-(2-chloroacetamidothiazol-4-yl)-2-(syn)-methoxyiminoacetic acid or an alkali metal or amine salt thereof is reacted with an N-methyldithiocarbamic acid alkali metal salt, or an N-ethyldithiocarbamic acid alkali metal salt.

7. A method as claimed in claim 1, wherein 2-(2-chloroacetamidothiazol-4-yl)-2-(syn)-methoxyiminoacetic acid is reacted with sodium N-methyldithiocarbamate.

8. A method as claimed in any one of claims 1 to 25, wherein the reaction is carried out in an inert solvent at a temperature between −10° C. and 50° C.

* * * * *